US012729405B2

(12) United States Patent
Yang et al.

(10) Patent No.: US 12,729,405 B2
(45) Date of Patent: Sep. 8, 2026

(54) METHOD AND KIT FOR DETERMINING BENEFIT OF CHEMOTHERAPY

(71) Applicant: St. Jude Children's Research Hospital, Inc., Memphis, TN (US)

(72) Inventors: Jun J. Yang, Memphis, TN (US); Jiyang Yu, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 1112 days.

(21) Appl. No.: 17/637,510

(22) PCT Filed: Aug. 24, 2020

(86) PCT No.: PCT/US2020/047604
§ 371 (c)(1),
(2) Date: Feb. 23, 2022

(87) PCT Pub. No.: WO2021/041299
PCT Pub. Date: Mar. 4, 2021

(65) Prior Publication Data

US 2022/0290251 A1 Sep. 15, 2022

Related U.S. Application Data

(60) Provisional application No. 62/893,289, filed on Aug. 29, 2019.

(51) Int. Cl.

| | |
|---|---|
| ***C12Q 1/6886*** | (2018.01) |
| ***A61K 31/5025*** | (2006.01) |
| ***A61K 31/506*** | (2006.01) |
| ***A61P 35/02*** | (2006.01) |
| ***G01N 33/575*** | (2026.01) |

(52) U.S. Cl.
CPC ........ *C12Q 1/6886* (2013.01); *A61K 31/5025* (2013.01); *A61K 31/506* (2013.01); *A61P 35/02* (2018.01); *G01N 33/5758* (2026.01); *C12Q 2600/106* (2013.01); *C12Q 2600/158* (2013.01); *G01N 2333/912* (2013.01); *G01N 2440/14* (2013.01)

(58) Field of Classification Search
None
See application file for complete search history.

(56) References Cited

U.S. PATENT DOCUMENTS

| | | | |
|---|---|---|---|
| 2010/0004257 | A1 | 1/2010 | Haura |
| 2010/0120788 | A1 | 5/2010 | Wang et al. |
| 2011/0166154 | A1 | 7/2011 | Slamon et al. |
| 2013/0071860 | A1 | 3/2013 | Hale et al. |
| 2013/0244936 | A1 | 9/2013 | Goffin et al. |
| 2016/0349256 | A1 | 12/2016 | James et al. |

FOREIGN PATENT DOCUMENTS

| | | | | |
|---|---|---|---|---|
| WO | WO-2008153743 | A2 * | 12/2008 | ......... C07K 14/4746 |
| WO | 2010138843 | A2 | 12/2010 | |

OTHER PUBLICATIONS

Serafin et al. (Blood Dec. 2017 vol. 130 p. 2750) (Year: 2017).*
Bommhardt et al. (2019) "Beyond TCR Signaling: Emerging Functions of Lck in Cancer and Immunotherapy," Int. J. Mol. Sci. 20(14):3500.
Frismantas, et al. (2017) "Ex vivo drug response profiling detects recurrent sensitivity patterns in drug-resistant acute lymphoblastic leukemia," Blood 129(11):e26-e37.
Guerrouahen et al. (2009) "Flow Cytometric Determination of Src Phosphorylation in Pediatric Patients Treated with Dasatinib," Pediatr. Blood Cancer 53(6):1132-35.
International Preliminary Report on Patentability in PCT/US2020/047604, dated Mar. 10, 2022.
International Search Report and Written Opinion in PCT/US2020/047604, dated Jan. 14, 2021.
Pemovska, et al. (2015) "Axitinib effectively inhibits BCR-ABL1(T315I) with a distinct binding conformation," Nature 519(7541):102-105.
Singh et al. (2018) "Exploration of the therapeutic aspects of Lck: A kinase target in inflammatory mediated pathological conditions," Biomed. Pharmacother. 108:1565-1571.
Verma et al. (2014) "Philadelphia chromosome positive pre-T cell acute lymphoblastic leukemia: a rare case report and short review," Indian J. Hematol. Blood Transfus. 30(Suppl. 1):S177-179.

* cited by examiner

*Primary Examiner* — Katherine D Salmon
(74) *Attorney, Agent, or Firm* — Licata & Tyrrell P.C.; Jane Massey Licata

(57) ABSTRACT

Nucleic acid- and protein-based methods for identifying a patient sensitive to treatment with a tyrosine kinase inhibitor are provided, as is a method for treating a subject with a T-lineage hematological malignancy. Specifically, the method comprising determining activity levels of LCK nucleic acid or protein in a biological sample from a patient with a T-lineage hematological malignancy, wherein an increase in the activity levels of the LCK nucleic acid or protein in the biological sampled compared to a reference level indicates that the patient is sensitive to treatment with a tyrosine kinase inhibitor.

6 Claims, No Drawings

METHOD AND KIT FOR DETERMINING BENEFIT OF CHEMOTHERAPY

This application is a U.S. National Stage Application of PCT/US2020/047604 filed Aug. 24, 2020, which claims the benefit of priority of U.S. Provisional Application No. 62/893,289, filed Aug. 29, 2019, the contents of each of which are incorporated herein by reference in their entireties.

This invention was made with government support under grant no. GM115279 and GM134382 awarded by the National Institutes of Health. The government has certain rights in this invention.

INTRODUCTION

Background

The treatment of relapsed and refractory acute lymphoblastic leukemia (ALL) remains challenging. Progress in ALL genomics provides unprecedented insight into potentially actionable targets, such as activating mutations in tyrosine kinases RAS, or interleukin-7R. Recurrent features such as MLL-AF4 rearrangements, the TCF3-HLF fusion, and hypodiploid karyotypes define rare subgroups with highly drug-resistant disease. However, a majority of patients who may benefit from innovative therapies are still identified on the basis of the persistence of minimal residual disease or failure of remission induction therapy.

Dasatinib and ponatinib are orally active, multi-targeted tyrosine kinase inhibitors (TKIs) of the ABL and Src family kinases. Dasatinib and ponatinib have been approved by the FDA for the treatment of chronic myelogenous leukemia (CML) and Philadelphia chromosome-positive (Ph+) ALL. However, critical to the use of these drugs is the identification of patients most likely to respond to treatment. While diagnostic methods for assessing the use of such drugs in the treatment of cancer have been suggested in US 2011/0166154 A1 and US 2010/0004257 A1, an indication of whether these drugs can provide efficacy in the treatment of a T-lineage hematological malignancy has not been demonstrated. Further, expression levels of SLC2A3, ITPR1, TCF4, and FLT3 have been suggested for use in evaluating whether a patient with ALL is likely to respond to imatinib or dasatinib (WO 2010/138843 A2). However, the use of these markers in other T-lineage hematological malignancies was not demonstrated.

Large integrative studies on cell line panels illustrate the difficulty of extrapolating drug responses on the basis of genomic data even when indicative lesions in druggable pathways occur. Moreover, such alterations may be over- or underrepresented in cell lines, whereas patient-derived xenografts (PDXs) seem to reproduce the genetic driver mutation landscape in leukemia more closely (Frismantas, et al. (2017) *Blood* 129(11):e26-e37). To obtain insight into interpatient drug response heterogeneity, an in vitro platform has been developed directly using patient-derived leukemia cells. Drug sensitivity testing has revealed individual drug response phenotypes in acute myeloid leukemia (AML) (Pemovska, et al. (2013) *Cancer Discov.* 3(12):1416-1429) and identified new strategies to bypass resistance to tyrosine kinase inhibitors (TKIs) in patients with deleterious BCR-ABL mutations (Pemovska, et al. (2015) *Nature* 519(7541): 102-105).

SUMMARY OF THE INVENTION

This invention provides a method of identifying a patient sensitive to treatment with a tyrosine kinase inhibitor by determining activity levels of a LCK nucleic acid or protein in a biological sample from a patient with a T-lineage hematological malignancy, wherein an increase in the activity levels of the LCK nucleic acid or protein in the biological sampled compared to a reference level indicates that the patient is sensitive to treatment with a tyrosine kinase inhibitor. In one embodiment, the T-lineage hematological malignancy is T-cell acute lymphoblastic leukemia. In another embodiment, the tyrosine kinase inhibitor is dasatinib or ponatinib. In one aspect, the activity of the LCK nucleic acid is determined by calculating an activity score based upon a transcriptomic profile of the patient, wherein said method can optionally include determining an activity level of CD28, CD3E, CD40LG, CD3G, ICOS, and/or PTCRA nucleic acids. In another aspect, the activity of the LCK protein is determined by measuring phosphorylation levels of the LCK protein with a phospho-specific antibody via flow cytometry, wherein said method can optionally include determining an activity level of CD247 and/or ZAP70 protein.

A kit for identifying a patient sensitive to treatment with a tyrosine kinase inhibitor is also provided. In particular, such a kit includes antibodies that specifically bind to p-CD247, p-ZAP70 and p-LCK.

This invention also provides a method for treating a subject with a T-lineage hematological malignancy by administering to a subject a tyrosine kinase inhibitor that ameliorates a T-lineage hematological malignancy, wherein the subject has been determined to have, in a biological sample obtained from the subject, an increase in activity of at least LCK nucleic acid or protein relative to a reference level of LCK nucleic acid or protein. In one embodiment, the T-lineage hematological malignancy is T-cell acute lymphoblastic leukemia. In another embodiment, the tyrosine kinase inhibitor is dasatinib or ponatinib. In one aspect, the activity of the LCK nucleic acid is determined by calculating an activity score based upon a transcriptomic profile of the patient, wherein said method can optionally include determining an activity level of CD28, CD3E, CD40LG, CD3G, ICOS, and/or PTCRA nucleic acids. In another aspect, the activity of the LCK protein is determined by measuring phosphorylation levels of the LCK protein with a phospho-specific antibody via flow cytometry, wherein said method can optionally include determining an activity level of CD247 and/or ZAP70 proteins.

DETAILED DESCRIPTION OF THE INVENTION

Both dasatinib and ponatinib are FDA-approved agents for CML and Ph+ ALL. Existing biomarkers for dasatinib and ponatinib are based on ABL-translocation or fusion rearrangements; however, these genomic alternations are rare (<2%) in T-ALL. A transcriptomics-based (RNA-seq) predictive biomarker panel has now been developed to predict sensitivity of patients with T-cell acute lymphoblastic leukemia (T-ALL), as well as other T-lineage hematological malignancies, to treatment with tyrosine kinase inhibitors such as dasatinib and ponatinib. Use of the present biomarker panel indicates that up to 40% of patients with T-ALL are sensitive to dasatinib and ponatinib. This transcriptomics-based biomarker panel is the first to predict patient response to these two tyrosine kinase inhibitors and select beneficial patients most of whom do not have ABL-rearrangements.

In addition to a transcriptomics or nucleic acid-based biomarker panel, a protein phosphorylation-based assay has been developed to predict sensitivity of patients with T-ALL, as well as other T-lineage hematological malignancies, to treatment with tyrosine kinase inhibitors such as dasatinib and ponatinib. Applying flow cytometry to a panel of seven proteins involved in the T cell receptor signaling pathway, activity (i.e., phosphorylation) of these molecules is directly measured. Collectively, the phosphorylation of this panel of proteins can predict the sensitivity of a patient with T-ALL to dasatinib and other related drugs (e.g., ponatinib).

Accordingly, this invention provides transcriptomics- and/or protein-based methods for identifying a patient that is sensitive to treatment with a tyrosine kinase inhibitor. For the purposes of this invention, a "patient" or "subject" is meant to be any single subject, including humans, cattle, dogs, guinea pigs, rabbits, chickens, and so on, that has been diagnosed with a T-cell malignancy including leukemias, lymphomas, and myelomas, including acute, chronic, lymphocytic and/or myelogenous leukemias. In particular, a subject of the invention may have a T-ALL, T-cell lymphoma, adult T-cell lymphoma/leukemia, angio immunoblastic T-cell lymphoma, intestinal T-cell lymphoma, precursor T-lymphoblastic lymphoma, T-lymphoblastic and lymphoma/leukemia (T-Lbly/T-ALL), peripheral T-cell lymphoma, cutaneous T-cell lymphoma (CTLC; also called mycosis fungoides or Sezary syndrome), T-prolymphocytic leukemia (T-PLL) including of the small cell and cerebriform cell type, large granular lymphocyte leukemia (LGL) of the T-cell type; T-NHL hepatosplenic lymphoma; peripheral/post-thymic T cell lymphoma (pleomorphic and immunoblastic subtypes); and angiocentric (nasal) T-cell lymphoma. In certain embodiments, the subject has T-cell acute lymphoblastic leukemia.

As used herein, the term "biological sample" refers to a fluid containing cells and compounds of biological origin, and may include blood, bone marrow, stool or feces, lymph, urine, serum, plasma, pus, saliva, seminal fluid, tears, urine, bladder washings, colon washings, sputum or fluids from the respiratory, alimentary, circulatory, or other body systems. In particular embodiments, the "biological sample" is blood, e.g., whole blood, plasma or serum. In certain aspects of the current methods, any medical professional such as a doctor, nurse or medical technician may obtain a biological sample for testing. Alternatively, the patient or subject may obtain a biological sample for testing without the assistance of a medical professional, such as obtaining a whole blood sample, a urine sample, a fecal sample, a buccal sample, or a saliva sample.

A "biomarker" or "marker" refers to a molecular indicator that is associated with a particular pathological or physiological state. The biomarkers used herein are molecular indicators for T-lineage hematological malignancies. The term "biomarker panel" refers to a specified set of nucleic acids (in particular mRNAs) or proteins whose respective activity levels or phosphorylation states are collectively an indicator for, or predictive of, treatment efficacy with a tyrosine kinase inhibitor. Exemplary biomarker nucleic acids and proteins are set forth in Tables 1 and 2, respectively.

TABLE 1

| Nucleic Acid | Full Name | Entrez Gene ID No. | GENBANK Accession No.* |
|---|---|---|---|
| LCK | LCK proto-oncogene, Src family tyrosine kinase | 3932 | NM_001042771.2 |
| PTCRA | Pre T Cell Antigen Receptor Alpha | 171558 | NM_001243168.1 |
| CD28 | T-cell-specific surface glycoprotein CD28 | 940 | NM_006139.4 |
| IL4 | Interleukin 4 | 3565 | NM_000580.1 |
| PDCD1 | Programmed Cell Death 1 | 5133 | NM_005018.3 |
| CD3E | T-cell surface glycoprotein CD3 epsilon chain | 916 | NM_000733.3 |
| CD40LG | CD40 Ligand | 959 | NM_000074.2 |
| RASGRP1 | RAS Guanyl Releasing Protein 1 | 10125 | NM_005739.4 |
| CD3G | T-cell surface glycoprotein CD3 gamma chain | 917 | NM_000073.2 |
| ICOS | Inducible T-cell costimulator | 29851 | NM_012092.3 |
| ACVR2B | Activin receptor type-2B | 93 | NM_001106.4 |
| PIK3R3 | Phosphatidylinositol 3-kinase regulatory subunit gamma | 8503 | NM_003629.4 |

*Human reference sequence.

TABLE 2

| Protein | Full Name | Entrez Gene ID No. | GENBANK Accession No.* |
|---|---|---|---|
| SRC | Proto-oncogene tyrosine-protein kinase Src | 6714 | NP_938033 |
| CD247 | T-cell surface glycoprotein CD3 zeta chain | 919 | NP_00725 |
| ZAP70 | Zeta chain of T cell receptor associated protein kinase 70 | 7535 | NP_001070 |
| ITK | IL2 inducible T cell kinase | 3702 | NP_005537 |
| LCK | LCK proto-oncogene, Src family tyrosine kinase | 3932 | NP_001036236 |
| SLP76 | Lymphocyte cytosolic protein 2 or SH2 domain-containing leukocyte protein of 76 kDa | 3937 | NP_005556 |
| LAT | Linker for activation of T cells | 27040 | NP_001014989 |
| STAT5 | Signal transducer and activator of transcription 5 | 6776/6777 | NP_001275647/ NP_036580 |
| NFκB | Nuclear factor kappa B | 4790 | NP_003989/ NP_002493 |

*Human reference sequence.

In one aspect, the at least one biomarker is LCK nucleic acid and/or protein. In another aspect, the at least one biomarker is LCK nucleic acid and one or a combination of CD28, CD3E, CD40LG, CD3G, ICOS, and PTCRA. In a further aspect, the at least one biomarker is an LCK nucleic acid and one or a combination of PTCRA, CD28, IL4, PDCD1, CD3E, CD40LG, RASGRP1, CD3G, ICOS, ACVR2B, and PIK3R3 nucleic acids. Ideally, methods of this invention employ the use of a biomarker panel comprising or consisting of LCK, CD28, CD3E, CD40LG, CD3G, ICOS, and/or PTCRA nucleic acids.

In another aspect, the at least one biomarker is LCK protein and one or a combination of CD247 and ZAP70 proteins. In a further aspect, the at least one biomarker is LCK protein and one or a combination of SRC, CD247, ZAP70, ITK, SLP76, LAT, STAT5, and NFκB proteins. Ideally, methods of this invention employ the use of a biomarker panel comprising or consisting of LCK, CD247 and/or ZAP70 proteins.

In accordance with one aspect of this invention, the level of activity of a biomarker/biomarker panel of nucleic acids in a biological sample is determined or measured. Measuring or determining activity levels of a nucleic acid can be accomplished by a variety of different chemical and/or enzymatic reactions. In certain embodiments, methods may involve, but are not be limited to, next generation sequencing, single-molecule real-time sequencing, mass spectrometry, digital color-coded barcode technology analysis, microarray expression profiling, quantitative PCR, reverse transcriptase PCR, reverse transcriptase real-time PCR, quantitative real-time PCR, end-point PCR, multiplex end-point PCR, cold PCR, ice-cold PCR, in situ hybridization, northern hybridization, hybridization protection assay (HPA), branched DNA (bDNA) assay, rolling circle amplification (RCA), single molecule hybridization detection, invader assay, and/or Bridge Litigation Assay. Other non-limiting amplification methods may include real-time PCR (quantitative PCR (q-PCR)), digital PCR, nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. The activity level of biomarkers of a biomarker panel can be determined simultaneously or sequentially.

The methods may involve isolating nucleic acids such as ribonucleic acids from the biological sample, amplifying the nucleic acids and/or contacting or hybridizing one or more probes to an amplified or non-amplified nucleic acid. In certain embodiments, a microarray may be used to measure or determine the level of mRNA expression in a sample. Methods and compositions for isolating, enriching, and/or labeling mRNA molecules and for preparing and using probes, primer and/or arrays or other detection techniques for mRNA analysis are described in the art.

In some embodiments, the level of activity of a biomarker panel of nucleic acids is determined or measured by contacting the nucleic acids with a hybridizing agent (e.g., a probe or primer, or microarray containing a probe) and detecting hybridization between the nucleic acids and the hybridizing agent.

More particularly, the present invention includes a method for identifying a patient sensitive to treatment with a tyrosine kinase inhibitor by obtaining the transcriptome of a patient; analyzing a biomarker within the transcriptome; and determining the patient's sensitivity to treatment with a tyrosine kinase inhibitor based on the presence, absence or level of expression of the marker within the transcriptome. In certain embodiments, the transcriptome profile (i.e., whole mRNA expression/activity profile) is normalized and then input into a statistical algorithm, which generates a single score (termed the activity score) as an output that classifies the likely responsiveness of the patient to administration of a tyrosine kinase inhibitor. As used herein, the term "score" or "profile" includes any set of data that represents the distinctive features or characteristics associated with sensitive to treatment with a tyrosine kinase inhibitor. Advantageously, the transcriptome or mRNA expression profile of a subject may be acquired using standard RNA-Seq technology or microarray and the activity score of a biomarker can be calculated by known methods. See, e.g., WO 2017/070441 A1; Efron & Tibshirani (2007) *Ann. Appl. Stat.* 1:107-129) and Example 1 herein.

Once measured, the methods further include the step of comparing the level of activity of the biomarker/biomarker panel nucleic acids in the biological sample to a reference level of the same biomarker/biomarker panel nucleic acids in one or more healthy subjects to determine a biomarker difference value. The reference level may be from a single healthy individual or from a collection of individuals, e.g., in a database.

A difference between activity levels may be at least, or be at most, about 2-, 3-, 4-, 5-, 10-, 20-, 30-, 40-, 50-, 60-, 80-, 90-, 100-, 110-, 120-, 130-, 140-, 150-, 160-, 170-, 180-, 190-, 200-, 250-300-, 350-, 400-, 450-, 500-, 600-, 700-, 800-, 900-, or 1000 times or -fold (or any range derivable therein). In particular embodiments, a level of biomarker activity is increased in the biological sample compared to a reference level if it is at least 5-, 10-, 20-, 30-, 40-, 50-, 60-, 80-, 90-, 100-, 110-, 120-, 130-, 140-, 150-, 160-, 170-, 180-, 190-, 200-, 250-300-, 350-, 400-, 450-, 500-, 600-, 700-, 800-, 900-, or 1000-fold higher or lower (or any range derivable therein), respectively, than the reference level. This may or may not include using a standardized or normalized level of activity in determining whether there is an increase. A measured increase in the activity of at least LCK and optionally one or a combination of CD28, IL4, PDCD1, CD3E, CD40LG, RASGRP1, CD3G, ICOS, ACVR2B, PTCRA and PIK3R3 as compared to the reference levels indicates that the patient from whom the biological sample was obtained is sensitive to treatment with a tyrosine kinase inhibitor, i.e., the patient will receive a benefit from such treatment. In particular embodiments, the subject is sensitive or will respond to treatment with dasatinib or ponatinib.

In accordance with another aspect of this invention, the phosphorylation of a biomarker protein in a biological sample is determined or measured. Measuring or determining the phosphorylation status of a protein can be accomplished by a variety of cellular assays, including whole or fixed-cell assays, or cell lysate assays. In certain embodiments, methods may include, but are not be limited to, the use of panels of phospho-specific antibodies in assays of cellular content, such as immunohistochemical (IHC) assays, flow cytometric (FC) assays, immunofluorescent (IF) assays, capture-and-detection assays, reversed phase assays, and the like.

Cellular analysis, and in particular IHC and flow cytometry, is an accepted clinical procedure (advantageous for clinical/prognostic assays), and enables examination of protein activity at the cell or tissue level (as opposed to protein expression), including the ability to rapidly analyze multiple sequential tissue slices or cells in parallel. In addition, particular cells having activated proteins can be identified, and can, therefore, be directly compared to normal cells to identify differences in in vivo signaling. Further, protein localization within a cell may be determined, in addition to phosphorylation status.

Accordingly, in one embodiment, the invention provides a method for identifying a patient sensitive to treatment with a tyrosine kinase inhibitor by obtaining a biological sample from a patient with a T-lineage hematological malignancy; and using a phospho-specific antibody in a cellular assay to detect the phosphorylation status of a cognate biomarker protein in the biological sample, wherein the biomarker panel is at least LCK and may optionally include one or a combination of SRC, CD247, ZAP70, ITK, SLP76, LAT, STAT5, and NFκB. Phosphorylation (i.e., activation) of one or more of biomarker proteins indicates that the patient from whom the biological sample was obtained is sensitive to treatment with a tyrosine kinase inhibitor, i.e., the patient will receive a benefit from such treatment. In particular embodiments, the subject is sensitive or will respond to treatment with dasatinib or ponatinib.

A "phospho-specific antibody" means an antibody, whether polyclonal or monoclonal, that binds to a target protein only when phosphorylated at a particular residue or site, and does not substantially bind to the protein when not phosphorylated at that residue or site, or to proteins other than the target protein; the term encompasses humanized antibodies, antibody binding fragments, recombinant antibodies, and the like. In accordance with this invention, virtually any phospho-specific antibody capable of detecting a desired protein when phosphorylated at a particular residue or site may be used. Phospho-specific antibodies are widely commercially available (e.g., from Cell Signaling Technology, Inc.; BioSource, Inc.; Santa Cruz Biotechnology, Inc.; Upstate Biotechnology, Inc.), and may also be produced by techniques well known in the art. Examples of phospho-specific antibodies of use in this invention are provided in Table 3.

TABLE 3

| Biomarker Protein | Phosphorylation Site-Specific Antibody |
| --- | --- |
| Src | Src-Y418 Antibody |
| | Src-Y530 Antibody |
| CD247 | CD247-Y72 Antibody |
| ZAP70 | Zap70-Y319 Antibody |
| | Zap70-Y352 Antibody |
| | Zap70-Y493 Antibody |
| ITK | Itk-Y551 Antibody |
| | Itk-Y511 Antibody |
| LCK | Lck-Y394 Antibody |
| | Lck-Y505 Antibody |
| SLP76 | Slp76-Y128 Antibody |
| LAT | Lat-Y171 Antibody |
| | Lat-Y226 Antibody |
| STAT5 | Stat5-S694 Antibody |
| | Stat5-S780 Antibody |
| NFκB | NFκB p100-S870 Antibody |
| | NFκB p105-S907 Antibody |
| | NFκB p105-S927 Antibody |
| | NFκB p105-S932 Antibody |
| | NFκB p65-S276 Antibody |
| | NFκB p65-S468 Antibody |
| | NFκB p65-S529 Antibody |
| | NFκB p65-S536 Antibody |

Panels of phospho-specific antibodies used may also include additional non-phospho-specific antibodies or reagents. For example, other modification-specific antibodies may be included, such as acetylation- or nitrosylation-specific antibodies, to detect activation of signal transduction targets having such modifications. Control antibodies may also be included, for example, protein-specific antibodies that detect merely the presence of a given protein (not its modification status), or site-specific antibodies that detect a target in its unphosphorylated form. Additional non-phospho-specific antibodies or reagents, or phospho-specific antibodies to targets other than the biomarkers disclosed herein, may also be employed in the predictive methods of the invention.

Phosphorylation status in a cellular sample is examined using phospho-specific antibodies in a cellular assay, namely, any assay suitable for detecting in vivo protein activity in a particular cell. Examples of suitable cellular assays include the following preferred assays: immunohistochemistry (IHC), flow cytometry (PC), immunofluorescence (IF) (all of which are whole cell or tissue-based staining assays), and capture-and-detection (e.g., ELISA), or reversed phase assays (which are cell-lysate based assays).

Immunohistochemical (IHC) staining of biological samples may be carried out according to well-known techniques. See, e.g., Antibodies: A Laboratory Manual, Chapter 10, Harlow & Lane Eds., Cold Spring Harbor Laboratory (1988). Briefly, a paraffin-embedded sample is prepared for immunohistochemical staining by deparaffinizing with xylene followed by ethanol; hydrating in water then PBS; unmasking antigen by heating slide in sodium citrate buffer; incubating the sample in hydrogen peroxide; blocking in blocking solution; incubating the slide in primary antibody (i.e., phospho-specific antibody) and secondary antibody; and finally detecting using, e.g., avidin/biotin.

Flow cytometry assay may also be used to determine the activation status of proteins. For example, bone marrow cells or peripheral blood cells from patients may be analyzed by flow cytometry for biomarkers of therapeutic response, as well as for other markers identifying various hematopoietic cell types. In this manner, activation status of malignant cells may be specifically characterized. Flow cytometry may be carried out according to standard methods. See, e.g. Chow, et al. (2001) Cytometry (*Communications in Clinical Cytometry*) 46:72-78. Briefly and by way of example, the following protocol for cytometric analysis may be used: fixation of the cells with 1% paraformaldehyde for 10 minutes at 37° C. followed by permeabilization in 90% methanol for 30 minutes on ice. Cells may then be stained with the primary phospho-specific antibody or antibodies, washed and labeled with a fluorescent-labeled secondary antibody. Alternatively, the cells may be stained with a fluorescent-labeled primary antibody. The cells would then be analyzed on a flow cytometer (e.g., a Beckman Coulter EPICS-XL) according to the specific protocols of the instrument used.

Immunoassay formats and variations thereof which may be useful for carrying out the methods disclosed herein are well-known in the art. See generally Maggio (1980) *Enzyme-Immunoassay*, CRC Press, Inc., Boca Raton, FL See also, e.g., U.S. Pat. Nos. 4,727,022; 4,659,678; and 4,376,110. Conditions suitable for the formation of reagent-antibody complexes are well-described. Monoclonal antibodies may be used, for example, in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of phosphorylated target is detectable compared to background.

Alternatively, the biomarkers may be analyzed in an ELISA or reverse-phase array format. For the ELISA format, a capture antibody for each biomarker is affixed to a solid substrate such as a plastic ELISA plate, nitrocellulose membrane or bead. The patient sample is incubated with the labeled substrate allowing for the capture of the biomarker proteins to the substrate via the capture antibodies. The substrate is then washed. The captured proteins are then detected using a second antibody specific for each protein. The bound detection antibody may be detected by a labeled secondary antibody or by labeling (fluorescent or enzyme) the detection antibody.

In the reverse phase method, lysates of patient samples are fixed to a solid substrate in predetermined locations. The fixed sample is then incubated with the antibodies. After washing, the bound antibodies are detected by various detection methods such as secondary detection antibodies or by prelabeling the antibodies with fluorescent labels.

Phospho-specific antibodies employed in the methods of the invention may be conjugated to a solid support suitable for a diagnostic assay (e.g., beads, plates, slides or wells formed from materials such as latex or polystyrene) in accordance with known techniques, such as precipitation. Antibodies or equivalent binding reagents, may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Alternatively, phospho-specific antibodies employed in cellular assays may be optimized for use in other clinically-suitable applications, for example bead-based multiplex-type assays, such as IGEN, Luminex™ and/or Bioplex™ assay formats, or otherwise optimized for antibody arrays formats.

The invention provides, in part, kits for carrying out a method disclosed herein. In particular, the kit is used to evaluate one or more protein biomarkers. In certain embodiments, a kit contains a panel of phospho-specific antibodies against phosphorylated p-CD247, p-ZAP70, and p-LCK; and one or more additional reagent(s) suitable for detecting binding of the antibodies to said protein in a cellular assay. In other embodiments, a kit contains a panel of phospho-specific antibodies against phosphorylated (p)-Src, p-CD247, p-ZAP70, p-ITK, p-LCK, p-SLP76, p-LAT, p-LAT, p-STAT5, and p-NFκB; and one or more additional reagent(s) suitable for detecting binding of the antibodies to said protein in a cellular assay. The kit may include any one or more of the following materials: enzymes, reaction tubes, buffers, and detergents. In a particular embodiment, the kit allows a practitioner to obtain samples of blood or serum. Instructions for performing an assay can also be included in the kits.

The components of the kits may be packaged either in aqueous media or in lyophilized form. The container means of the kits will generally include at least one vial, test tube, flask, bottle, syringe or other container means, into which a component may be placed. Where there is more than one component in the kit, the kit also will generally contain a second, third or other additional container into which the additional components may be separately placed. However, various combinations of components may be included in a vial.

Once a patient has been identified, in accordance with the diagnostic methods herein, as being sensitive to treatment with a tyrosine kinase inhibitor, the subject may be administered a tyrosine kinase inhibitor that ameliorates a T-lineage hematological malignancy. Accordingly, this invention also provides a method for treating a subject with a T-lineage hematological malignancy by administering to the subject a tyrosine kinase inhibitor that ameliorates a T-lineage hematological malignancy, wherein the subject has been determined to have in a biological sample obtained from the subject an increase in activity of at least LCK nucleic acid or protein relative to a reference level of LCK nucleic acid or protein and optionally CD28, CD3E, CD40LG, CD3G, ICOS, and PTCRA nucleic acids and/or CD247 and ZAP70 proteins. In some embodiments, the method further includes that the subject has an increase in the activity of at least one of IL4, PDCD1, RASGRP1, ACVR2B, and PIK3R3 nucleic acids and/or ITK, SLP76, LAT, STAT5, and NFκB proteins. In certain embodiments, the T-lineage hematological malignancy is T-cell acute lymphoblastic leukemia.

Methods for treating a subject suffering from a T-lineage hematological malignancy can include the steps of determining whether a biological sample obtained from the individual exhibits an increase in activity relative to a reference level of at least LCK nucleic acid or protein and optionally CD28, CD3E, CD40LG, CD3G, ICOS, and PTCRA and/or CD47 and ZAP70 proteins; and administering a therapeutically effective amount of a tyrosine kinase inhibitor to the subject. The therapeutically effective amount may depend upon the type of T-lineage hematological malignancy as well as the age and condition of the subject being treat as well as whether or not the tyrosine kinase inhibitor therapy will be combined with a second therapy.

Suitable tyrosine kinase inhibitors of use in the treatment of T-lineage hematological malignancy include but are not limited to dasatinib, ponatinib, imatinib, bosutinib, nilotinib, sorafenib, sunitinib and derivatives thereof. In particular embodiments, the tyrosine kinase inhibitor is dasatinib or ponatinib.

Amounts of tyrosine kinase inhibitors effective to treat cancer can broadly range between about 10 mg and about 150 mg per day, more generally range between about 35 mg and about 140 mg per day, and preferably between about 70 mg and about 140 mg per day (administered orally twice a day). The rationale for the preferred dose range is based upon dasatinib (BMS-354825) dosing for CML and the clinical pharmacology data presented in "Dasatinib (BMS-354825) Oncologic Drug Advisory Committee (ODAC) briefing document, NDA-21-986, in which the Cmax was between approximately 60-120 nM.

The second therapy can be any therapy effective in treating the disorder, including, for example, therapy with another protein kinase inhibitor. The dose of tyrosine kinase inhibitor can remain the same, be reduced, or be increased when combined with a second therapy.

The following non-limiting examples are provided to further illustrate the present invention.

Example 1: Materials and Methods

Patients and Samples. The ALL pharmacotyping cohort was composed of 352 ALL patients tested for leukemia sensitivity to dasatinib ex vivo: 113 pediatric cases from the Total Therapy XVII trial at St. Jude Children's Research Hospital (Clinicaltrials.gov ID NCT03117751); and 239 adults from MD Anderson Cancer Center, University of Chicago, ECOG E1910 clinical trial (clinicaltrials.gov NCT02003222), and the Alliance A041501 trial (clinicaltrials.gov NCT03150693). Immunophenotype was determined at diagnosis, with 307 and 45 B-ALL and T-ALL cases, respectively.

Leukemia blasts were obtained from either bone marrow or peripheral blood after gradient centrifugation using a high-density solution sold under the tradename FICOLL®. Samples were subjected to further enrichment by magnetic-activated cell sorting if blast percent was below 85% (CD19 for B-ALL and CD7 for T-ALL, respectively). Bone marrow or blood collected during remission were used as germline samples. DNA was extracted using Blood & Cell Culture DNA Midi Kit (Qiagen) or QIAAMP® DNA Blood Midi Kit (Qiagen), and RNA was prepared using the RNEASY® Mini Kit (Qiagen).

Genomic Profiling. Total RNA-seq was performed for leukemia only: total RNA library was constructed using ILLUMINA® TrueSeq stranded mRNA library prep kit and sequenced using the HISEQ® 2000/2500 or NOVASEQ® 6000 platform (2×101-bp pair-end reads). On average, at least 10× coverage was achieved for more than 43% of the transcriptome. Gene expression was quantified as Fragments Per Kilobase of transcript per Million mapped reads (FPKM) using RSEM v1.2.2884 under default parameters with the human genome (GRCh38) and annotation file (Gencode v30; Frankish, et al. (2018) *Nucl. Acids Res.* 47:D766-D773; Zhang, et al. (2015) *New Engl. J. Med.* 373:2336-2346). Gene level FPKM values were used for downstream analyses. Lowly-expressed genes were defined as those not expressed in more than half of the samples and genes with invariable expression were those with an inter-quartile range less than 0.4 after $\log_2$ FPKM+0.1) transformation, both of which were removed from subsequent analyses. Outliers were detected by principal component analysis, distance estimation, and density distribution evaluation. CICERO was used to detect fusions (Qian, et al. (2017) *Genome Res.* 27:185-195). The reported fusion contigs were remapped by BLAT to check reliability of mapping quality, breakpoints were manually reviewed from the aligned reads.

Whole exome or whole genome seq was performed for matched germline-leukemia pairs, respectively. For whole exome seq, library was prepared using the NEXTERA® rapid capture expanded exome kit and subjected to pair-end sequencing (101 bp read length) on the HISEQ® 2000/2500 or NOVASEQ® 6000 platform. On average, 20× coverage was achieved for a median of 71% exome in both leukemia and germline genomes. For whole genome seq, libraries were constructed using KAPA® Hyperprep kit (Roche) according to manufacturer's protocols and sequenced via HISEQ® 2000/2500 and NOVASEQ® 6000 (2×151 bp pair-end reads). Whole exome seq and whole genome seq analyses were performed following procedures established previously (Li & Durbin (2009) *Bioinformatics* 25:1754-1760). Reads were aligned to the human reference genome GRCh37 by BWA (version 0.7.12; McKenna, et al. (2010) *Genome Research* 20:1297-1303). Picard (version 1.129) was used for marking PCR duplication. Afterwards, the reads were realigned around potential indel regions by GATK IndelRealigner module (version 3.5) following the recommended procedures (DePristo, et al. (2011) *Nat. Genet.* 43:491-8). The MuTect2 module from GATK was used to identify single nucleotide variants and indels from matched leukemia and germline samples (Wang, et al. (2010) *Nucl. Acids Res.* 38:e164). Variants with any of the following features in the tumor data were excluded: 1) read depth <20; 2) mutant allele frequency <10%; 3) all reads supporting mutation calls coming from the same mapping direction; and 4) two or more mutation called in the same sample within a 30 bp window. Remaining high quality variants were then annotated by ANNOVAR (Chen, et al. (2015) *Nat. Methods* 12:527-30). Tumor copy-number variations and structural variations were detected using CONSERTING (Wang, et al. (2011) *Nat. Methods* 8:652-4) and CREST (Ritchie, et al. (2015) *Nucl. Acids Res.* 43:e47).

For five cases with leukemia RNA-seq data only and eight cases with leukemia whole exome-seq data only, the GATK pipeline was also used to infer single nucleotide variants and indels from RNA-Seq with the HaplotypeCaller module (DePristo, et al. (2011) *Nat. Genetics* 43:491-8). Variants called in genes in which mutations were detected in other cases by paired whole genome or whole exome seq were also included.

The previously published RNA-seq data from the TARGET T-ALL cohort (N=261; Liu, et al. (2017) Nat. Genetics 49:1211-8) was used for network building and biomarker analyses as described below.

Ex vivo Leukemia Drug Sensitivity Assay. Drug response of primary human ALL cells was evaluated using a co-culture system and flow cytometry assays. hTERT-immortalized mesenchymal stem cells (Benjamini & Hochberg (1995) *J. Royal Stat. Soc. Series B* 57:289-300; Wang, et al. (2019) *Nat. Commun.* 10:3718) were first seeded in a 96-well plate format at a density of 10,000 cells per well in 100 μL of complete medium (RPMI-1640, L-glutamine, 10% fetal bovine serum and 1 μM Hydrocortisone). After 24 hours, leukemia cells were added at 160,000 cells per well to the stromal cell layer in 80 μL AIM-V medium along with 20 μL of drug solution prepared in the same medium. Duplicates were included for each of the six drug concentrations (10000, 1000, 100, 10, 1, 0.1 nM for dasatinib/ponatinib/nilotinib; 2500, 250, 25, 2.5, 0.25, 0.025 nM for imatinib). After 96 hours incubation at 37° C. with 5% $CO_2$, cells were harvested and stained with CD19 or CD7 to identify leukemia blasts (for B-ALL and T-ALL, respectively). The total number of live leukemia cells were evaluated by using flow cytometry after Annexin V and DAPI staining. Drug-induced death was estimated by comparing to leukemia cells treated with the vehicle alone. The drug concentration that killed 50% of the leukemia cells ($LC_{50}$ value) was determined using a dose-response model and as a measurement of drug sensitivity. Quality control was performed to remove cases with low viability (less than 1000 viable blast cells in each well in the absence of drugs on day 4). For cases with which even the lowest dasatinib concentration kills more than 50% of leukemia cells, $LC_{50}$ was assigned as 0.05 nM (half of the lowest drug concentration). Conversely, for cases with extreme resistance to dasatinib (i.e., >50% viability even at the highest drug concentration), $LC_{50}$ was assigned as 20000 nM (twice of the highest concentration tested).

Construction of T-ALL interactome via SJARACNe. To reverse engineer a T-ALL specific interactome (TALLi), SJARACNe (Khatamian, et al. (2019) *Bioinformatics* 35:2165-2166) with default parameters (bootstrap=100; consensus cluster P=10−5) was applied to the TARGET T-ALL RNA-seq dataset (Liu, et al. (2017) *Nat. Genet.* 49:1211-1218) with expression profile of 27,218 unique genes from 261 patients, after removing 5,820 genes with low or invariable expression across samples and also three cases identified as outliers. Based on Gene Ontology classification, a list of transcription factor genes and signaling molecule genes (N=2,002 and 9,626, respectively) was compiled. Transcription factor network and signaling molecule network were generated separately using SJARACNe, with master regulators (hubs) linked to their targets through interactions (edges) based on gene-gene relationship derived from their expression pattern. The transcription factor network contained 27,063 nodes (genes) and 484,160 edges; signaling network included 26,927 nodes (genes) and 584,068 edges. After combining these two networks, the final data-driven TALLi consisted of 35,102 nodes (genes) and 1,068,228 edges, among which, there were 7,924 unique hub genes, including 1,653 transcriptional factors and 6,271 signaling molecules.

Genome-Scale CRISPR-Cas9 Screen and Analysis. T-ALL cell lines HSB-2, PF-382, and SUP-T1 were first engineered to stably express Cas9. 293T cells were plated at a density of $1.5\times10^6$ cells per well (10 mL volume) 24 hours pre-transfection in a 10-cm dish. Transfection was performed using a transfection reagent sold under the tradename EUGENE® 6 (Promega Corporation, Madison WI) according to the manufacturer's protocol. Briefly, two solutions were prepared. One solution contained 24 μL of EUGENE® 6 diluted in 300 μL of culture media sold under the tradename OPTI-MEM® (Life Technologies, Carlsbad, CA) and incubated at room temperature for 5 minutes. The second solution contained 4000 ng pCMV-VSV-G (Addgene), 2000 ng pCMVdeltaR8.91, and 8000 ng pLX311-Cas9 (Addgene) or pXPR_011_EGFP (Addgene) in a final volume of 300 μL with culture media sold under the tradename OPTI-MEM®. The two solutions were combined and incubated at room temperature for 20-30 minutes. The transfection mixture was added dropwise to the 293T cells grown in 5.0 mL viral harvest media (RPMI 1640+10% FBS+1% BSA), and then plates were returned to 37° C. Virus was harvested 72 hours post-transfection. T-ALL cells ($4\times10^6$) were suspended in 100 μL of growth media, 100 μL of freshly isolated lentivirus and spin infected for 2 hours at 37° C. at 2,800×g. Anti-heparin compound sold under the tradename POLYBRENE® was added at the final concentration of 8 μg/mL (Sigma-Aldrich, St. Louis, MO). Cells were selected 72 hours later with 8 μg/mL blasticidin (for pLX311-Cas9 expressing cells) (Sigma-Aldrich, St. Louis, MO) or 1 μg/mL puromycin (Invitrogen, San Diego, CA) (for pXPR_011 expressing cells). Optimal infection conditions were determined for each T-ALL cell line in order to retain a Cas9 activity greater than 50%. In fact, in the presence of Cas9, PXPR_011 transduced T-ALL lines will no longer express EGFP as this vector delivers both EGFP and a guide targeting EGFP. The fraction of EGFP positive and EGFP negative (% Cas9 activity) was measured by flow cytometry using (Attune, Life Technologies, Carlsbad, CA).

Cas9-expressing T-ALL cell lines HSB-2, PF-382, and SUP-T1 were then used for the genome-scale CRISPR-Cas9 screen. This screen was conducted as previously described (Meyers, et al. (2017) *Nat. Genetics* 49:1779-1784) with data publicly available through the Dependency Map. To determine the genetic dependencies that were enriched in T-ALL cell lines, linear-model analyses from the limma R package (Wang, et al. (2015) *J. Proteome Res.* 14:829-838) were utilized to perform a two-tailed t-test for the difference in distribution of gene dependency scores in T-ALL cell lines compared to other cell lines screened. Statistical significance was calculated as a q-value derived from the p-value corrected for multiple hypothesis testing (Tan, et al. (2017) *Immunity* 46:488-503).

NetBID Analysis. After applying quality control on both drug sensitivity and RNA-seq data, 45 T-ALL were included in the NetBID analysis (Du, et al. (2018) *Nature* 558:141-5) to identify drivers of dasatinib sensitivity. Dasatinib $LC_{50}$ in ALL largely followed a bi-modal distribution, and sensitive and resistant were defined as $LC_{50}$ less or greater than 80 nM, respectively, with dasatinib $LC_{50}$ of BCR-ABL1 B-ALL as the reference. Therefore, subsequent analysis was performed comparing 15 sensitive vs 30 resistant T-ALL cases.

Expression profile was extracted from RNA-seq data for 18,294 genes and used for NetBID analysis. Then cal.Activity function (method='weightedmean') in NetBID was employed to infer the activities of master regulator genes for each patient from their gene expression profiles and the TALLi. The weighted mean activity of a hub (master regulator) gene i in sample s was defined by the following equation:

$$HUBsi = \frac{\sum_{j=1}^{n} SIGNij * MIij * EXPsj}{n}$$

The gene expression matrix was Z-normalized in each sample and EXPsj is the expression value of gene j in sample s. MIij is the mutual information between master regulator gene i and its target gene j and SIGNij is the sign of spearman correlation between gene i and its target gene j. The total number of targets for master regulator i is denoted by n.

To identify drivers of dasatinib sensitivity in T-ALL, differential activity (dasatinib sensitive cases vs. resistant cases) was calculated by NetBID function getDE.BID.2G and the P<10−5 was used as the significance cutoff. Pathway analysis was also performed to identify the enrichment of drivers in specific biological processes by querying the KEGG pathway database (Greuber, et al. (2013) *Nat. Rev. Cancer* 13:559-71; Konig, et al. (2008) *Cancer Res.* 68:9624-33) and evaluated the statistical significance of the enrichment using the Fisher's exact test. In addition, DrugBank (Wishart, et al. (2017) *Nucl. Acids Res.* 46:D1074-D1082), DGIdb (Cotto, et al. (2017) *Nucl. Acids Res.* 46:D1068-D1073), and chemical proteomics-based TKI target profiling (Klaeger, et al. (2017) *Science* 358 (6367):eaan4368) were also curated to compile a list of putative dasatinib targets whose enrichment in the 461 drivers was again evaluated by using the Fisher's exact test.

Dasatinib Biomarker Panel and Sensitivity Score. Given the significant enrichment of the known dasatinib target genes and genes in the preTCR pathway in the dasatinib sensitivity drivers identified by NetBID, a 30-gene biomarker panel was derived by filtering the 461 NetBID-predicted drivers against these two gene sets. To estimate biomarker-based dasatinib sensitivity score for a given patient, the RNA-seq profile ($\log_2$-transformed FPKM) was first standardized by z-transformation to make it comparable across samples, and then the activities of 30 drivers were individually calculated using T-ALLi and the cal.Activity function (method='weightedmean') in NetBID. For a given T-ALL case, a weighted (+1 for positive drivers and −1 for negative drivers) mean of activities of all 30 drivers was taken as the dasatinib sensitivity score.

$$Ss = \frac{\sum_{i=1}^{30} Zi * Dsi}{30}$$

Ss is the summarized dasatinib sensitivity score of sample s. Zi is the z score of driver i between sensitive and resistant samples and Dsi is the driver i activity in sample s.

Dasatinib sensitivity score was estimated for 261 cases in the TARGET T-ALL dataset (Liu, et al. (2017) *Nat. Genetics* 49:1211-8) and also 45 cases samples in the pharmacotyping T-ALL cohort. In addition, this biomarker model was also applied to the gene expression dataset of 23 unique mouse T cell populations (Mingueneau, et al. (2013) *Nat. Immunol.* 14:619-632), to infer dasatinib sensitivity across distinctive development stages.

Phospho-proteomics and Data Analyses. Human T-ALL cells (derived from 3 dasatinib-sensitive and 2 resistant cases) were selected for proteomic studies. A total of 20 million cells were incubated with 10 nM dasatinib or vehicle in 10-$cm^2$ petri dishes and incubated for one hour. Cells were then harvested and washed rapidly using phosphate-buffered saline (PBS) and cell pellets were placed in liquid nitrogen for 30 minutes and stored at −80° C. Proteomic assays were performed following previously published procedures with slight modification (Tan, et al. (2015) *Proteomics* 15:500-507). Briefly, cell pellets were lysed and digested into peptides (Niu, et al. (2017) *Anal. Chem.* 89:2956-63), which were then labeled with Tandem Mass Tag reagents after desalting (Wang, et al. (2014) MCP 13:3663-3673). Labeled samples were equally mixed and further fractionated by a basic pH reverse-phase liquid chromatography and enriched for phosphopeptide using $TiO_2$ (Li, et al. (2016) *J. Proteome Res.* 15:2309-2320), followed by acidic pH reverse-phase LC-MS/MS103. Collected raw data were searched against a species-specific database for phosphopeptide identification, site localization, and quantification using the JUMP software suite (Wang, et al. (2015) *J. Proteome Res.* 14:829-838; Li, et al. (2016) *J. Proteome Res.* 15:2309-2320; Hornbeck, et al. (2011) *Nucl. Acids Res.* 40:0261-270). A false discovery rate cutoff of 1% was applied using a target-decoy strategy (Ihaka & Gentleman (1996) *J. Comp. Graph. Stat.* 5:299-314), resulting in the quantification of 27,757 phosphopeptides. For redundant phosphosites mapped to multiple peptide fragments, the phosphopeptide with the most significant difference in dasatinib-treated vs. untreated T-ALL samples in the sensitive group was selected, which resulted in 21,450 unique phosphosites for subsequent analyses.

Given the interest in the kinome, kinase activity was inferred based on the substrate phosphorylation levels. Specifically, the PhosphoSitePlus database was used to define 10,594 kinase-substrate pairs, representing 359 human kinases. Of these, phosphorylation events were detected in the T-ALL phospho-proteome dataset, related to 1,223 pairs linked to 172 kinases. The activity of each kinase was estimated using the following equation:

$$Ki = \frac{\sum_{j=1}^{n} \log 2(pij)}{n}$$

The intensity of each phosphosite was $\log_2$-transformed and Z-normalized in each sample. Pij is the abundance of phosphosite j which is phosphorylated by the Kinase i. The kinase i activity can be defined by its ability to phosphorylate substrate sites, which was estimated by the mean intensity of the kinase substrate phosphosites.

The differential expression analysis in the NetBID package was used based on linear modeling to compare inferred kinase activity between dasatinib-treated and baseline samples in the dasatinib-sensitive or dasatinib-resistant group separately.

Phospho-Flow of LCK Signaling Molecules. Human leukemia cells were collected and incubated overnight, before exposed to 1, 10, and 100 nM dasatinib for one hour. Cells were then harvested and immediately resuspended in cold PBS. Pre-warmed (37° C.) Lyse/Fix buffer (BD Phosflow™) was added and cells were incubated at 37° C. for 10 minutes and fixed cells were premetallized by treatment in pre-chilled Perm Buffer III (BD Phosflow™) for 30 minutes on ice.

Fixed and permeabilized cells were stained with phospho-antibodies targeting SRC-Y418/LCK-Y394 (BD Phosflow™), CD247-Y142 (BD Phosflow™) and ZAP70-Y319 (BD Phosflow™) and then run on flow-cytometer (MACSQUANT® X Flow Cytometer, Miltenyi Biotec). All flow data were analyzed by FlowJo™.

Patient Derived Xenograft (PDX) and Evaluation Of Dasatinib Therapy. PDXs were developed for 11 T-ALL cases in this cohort, using NOD.Cg-Prkdc$^{scid}$ Il2rgt$^{tm1Wj1}$/SzJ (NSG) mice. All animal studies were approved by approved by the Institutional Animal Care and Use Committee of St. Jude Children's Research Hospital. For each case, primary human T-ALL cells were injected into female NSG mice between 8-12 weeks of age through tail vein (2 million cells/mouse, resuspended in 200 μl sterile PBS). Health status of all injected mice were monitored every day. Starting from two weeks after injection, peripheral blood was obtained by retro-orbital bleeding and subjected to flow cytometry to determine the level of human leukemia (humanCD45 and humanCD7 double positive) every other week. Mice were euthanized when leukemia reached 85% in blood or they became moribund. Upon sacrifice, human leukemia cells were harvested from spleen and bone marrow according to established methods. For samples with blast % below 85%, magnetic-activated cell sorting was used for enrichment.

Dasatinib efficacy was evaluated in vivo in 4 T-ALL PDX models. Dasatinib was dissolved in citric acid (Jena Bioscience) and was administrated at 10 mg/kg twice daily through oral gavage. Blood was collected weekly to determine leukemic burden (hCD45 and hCD7 double positive percentage). Mice with human blast percentage over 85% in blood were considered lethal in survival analysis and euthanized.

Functional Studies of SPI1 Fusion in T-ALL. To overexpress TCF7-SPI1 fusion gene, a MSCV-IRES-mCherry vector (originally from MSCV-IRES-GFP, Addgene) was used and cDNA for the fusion gene fragment was inserted therein. Virus was packaged and concentrated (ultracentrifugation) prior to use.

To isolate hematopoietic progenitor/stem cells, mouse (C57BL/6) bone marrow cells were harvested and resuspended in MACS buffer (2 mM EDTA/0.5% BSA/PBS). Cells were then stained with CD117 MicroBeads (Miltenyi Biotec) and positively sorted with magnetic columns (LS column, Miltenyi Biotec) and separator (QuadroMACS™ Separator, Miltenyi Biotec) to enrich CD117 positive cells. After overnight incubation, CD117 enriched cells were stained with antibodies against CD117 (BD Pharmingen) and Sca-1 (BD Pharmingen) and sorted (FACS) for double positive population (LSK cells). Sorted bone marrow cells (e.g., LSK cells) was loaded onto virus-coated plate and centrifuged at 423 g for 10 minutes at room temperature. The transduced LSK cells were incubated for 2 days and sorted (FACS) for mCherry positive cells.

To evaluate LSK cell differentiation in vitro, the OP9-DL1 co-culture assay was employed. OP9-DL1 cells were maintained in α-MEM media (Gibco) with 20% FBS and penicillin-streptomycin. LSK cells were resuspended in α-MEM media (20% FBS/penicillin-streptomycin/FLT3-ligand, 10 ng·ml$^{-1}$/IL-7, 10 ng·ml$^{-1}$) and plated on irradiated OP9-DL1 cells (20Gy).

To determine dasatinib sensitivity in each DN stage, mouse thymocytes were isolated from C57BL/6 thymus and DN cells were enriched by removing CD4/8 positive cells. DN cells were then allowed to grow in vitro for 2 days on supportive OP9-DL1 cells with and/or without dasatinib. Viable cell counts in all DN populations were measured by flow-cytometry and compared between dasatinib treated and untreated groups.

To validate the association of SPI1 fusion with dasatinib sensitivity, two additional human T-ALL cases with TCF7-

SPI1 fusion were identified at St. Jude and the Institute of Hematology and Blood Diseases Hospital, Chinese Academy of Medical Sciences.

Statistical analysis. All statistical tests were two-sided and were chosen according to data distribution as described wherever appropriate; the threshold for statistical significance was defined as $P<0.05$, after applying correction for multiple testing (if applicable). the Statistical analysis was conducted using R. In the treatment outcome analysis, event-free survival was considered as a time-to-event variable and its relation to the t-SNE-based clusters was assessed by using the Cox proportional hazard regression model adjusting for T-ALL molecular subtypes and genetic ancestry. Events included relapse, second cancers, death in remission, etc.

Cell Line and Chemicals. hTERT MSCs (Mesenchymal Stem Cell) were maintained in RPMI1640 (Gibco) supplemented with 10% FBS and 1 μM hydrocortisone; T-ALL cell lines Jurkat, CEM, RPMI-8402, MOLT-4 and DND-41 were maintained in RPMI1640 supplemented with 10% FBS; other T-ALL cell lines HSB-2, CTV-1 and ALL-SIL were maintained in RPMI1640 with 20% FBS. All cells were incubated at 37° C. with 5% $CO_2$.

All drugs (for in vitro or ex vivo study) were purchased from Selleckchem. Dasatinib, ponatinib, nilotinib, WH 4-023, nintedanib and bosutinib were dissolved in DMSO at the working concentration of 10 mM and stored at −80° C. Imatinib was dissolved at the working concentration of 5 mM and stored at −80° C.

Cell Line Drug Sensitivity Profiling using the MTT Assay. For T-ALL cell lines, MTT assay was used to determine their sensitivity to dasatinib and other tyrosine kinase inhibitors. On day 0, cells were collected and resuspended in RPMI1640 without phenol red (Lonza) supplemented by 10% FBS at the density of 400,000 cells/mL. An 80 μL cell suspension was then plated on round-bottom 96-well plate (32,000 cells/well). Drug stock was thawed at room temperature and working solution was made by serial dilution with medium and added to cell suspension in 96-well plate. Vehicle control and blank (medium control) were set appropriately. After 3 days incubation at 37° C./5% $CO_2$, 10 μL of MTT solution (ThermoFisher, dissolved in sterile PBS, 12 mM) was added to each well. Cells were then incubated at 37° C. with 5% $CO_2$ for 4-6 hours. On hundred μL of isopropanol (Sigma, supplemented with 0.04 N hydrogen chloride) was added and the mixture was kept at room temperature for 5 minutes before measuring the absorbance at 562 nm.

Example 2: Ex Vivo Pharmacotyping Reveals Dasatinib Response in T-ALL

To characterize the pattern of dasatinib response in ALL, a cohort of 352 children and adults with ALL for whom drug sensitivity was determined (measured as $LC_{50}$, the concentration at which 50% of leukemia cells were killed) was analyzed. This cohort was composed of 239 adults (18 T-ALL and 221 B-ALL) and 113 children (27 T-ALL and 86 B-ALL), representative of diverse molecular subtypes of ALL. Comprehensive genomic profiling was performed using multiple sequencing platforms (RNA-seq, whole exome seq, and/or whole genome seq).

Across ALL samples, a wide inter-patient variability in dasatinib sensitivity was observed, with a bimodal distribution representing cases with low $LC_{50}$ (mean at 5.92 nM [range 0.05 to 79.4]) or high $LC_{50}$ (12,046.2 nM [101.6 to 20,000]). In B-ALL, cases with a BCR-ABL1 fusion gene or fusions involving ABL class genes consistently exhibited high sensitivity to dasatinib in both children and adults. The frequency of BCR-ABL1 ALL was significantly higher in adults who consequently also showed a higher prevalence of dasatinib response than children with B-ALL. Based on dasatinib $LC_{50}$ distribution in BCR-ABL1 ALL, 80 nM was selected as the cutoff to define dasatinib-sensitive vs dasatinib-resistant ALL. In T-ALL, 15 (33.3%) cases were classified as dasatinib-sensitive, with a $LC_{50}$ range largely indistinguishable from that of BCR-ABL1 B-ALL. Surprisingly, none of dasatinib-sensitive T-ALLs harbored ABL class fusion genes. Dasatinib-sensitive T-ALL was also significantly over-represented in children relative to adults (44.4% and 16.7% of T-ALL, respectively, $P=0.063$ by Fisher's exact test). Testing three other ABL inhibitors in a subset of these primary T-ALL samples (N=18), it was observed that dasatinib-sensitive cases were universally resistant to ABL-specific inhibitors imatinib and nilotinib, but responded effectively to ponatinib which shares non-ABL targets with dasatinib ($P=0.048$ by Pearson correlation test). In addition, eight human T-ALL cell lines were profiled for their sensitivity to dasatinib in vitro. Of these, three exhibited extreme response: ALL-SIL cell line with NUP214-ABL fusion and HSB-2 and CTV-1 cell lines with TCR-LCK fusion. Taken together, these results strongly indicated an ABL-independent mechanism driving dasatinib sensitivity in a significant proportion of T-ALL.

Example 3: NetBID Analyses Identified PreTCR-LCK Activation as the Driver of Dasatinib Sensitivity in T-ALL To systematically examine biological factors underlying T-ALL response to dasatinib, a data-driven network inference algorithm (NetBID; Du, et al. (2018) *Nature* 558:141-145) was used to model signaling molecule activity from RNA-seq derived expression profiles. Using the SJARACNe algorithm (Khatamian, et al. (2019) *Bioinformatics* 35:2165-66), a T-ALL-specific interactome (T-ALLi) was reverse-engineered from the RNA seq dataset of 261 unselected childhood T-ALL cases in the previously published TARGET ALL cohort (Liu, et al. (2017) *Nat. Genetics* 49:1211-1218). The resultant T-ALL network was composed of 27,179 genes and 1,068,228 interactions, representing 7,924 master regulators and their downstream targets. Overlaying T-ALLi to the RNA-seq dataset of 15 dasatinib-sensitive T-ALL and 30 resistant cases, activity of each master regulator was inferred on the basis of the expression of its targets weighed by the interaction strength of each regulator-target pair. Compared to cases resistant to this drug, 193 master regulators showed a significantly higher activity in dasatinib-sensitive T-ALL, whereas 268 regulators were downregulated, at a P value threshold of $10^{-5}$. In particular, a remarkable enrichment of up-regulated genes was observed in the pre-TCR signaling pathway ($P=9.6\times10^{-21}$), signified by CD28, CD3E, CD3G, ICOS, CD40LG, LCK, and PTCRA. In parallel, a list of 94 putative dasatinib targets was manually curated using DrugBank, DGIdb and chemical proteomics-based tyrosine kinase inhibitor (TKI) target profiling. Of 13 targets identified in all three databases, four (SRC, LCK, FYN, and FGR) showed a significantly higher activity in dasatinib-sensitive T-ALL from the NetBID analyses and LCK was the top hit with the most pronounced difference. Collectively, these results indicated LCK as the potential driver for the observed dasatinib sensitivity in T-ALL.

To demonstrate this, seven dasatinib-sensitive and four resistant T-ALL cases were selected to establish patient-derived xenografts (PDXs), with which human leukemia cells were expanded for further functional experiments. Focusing on key components of the preTCR pathway immediately up- and down-stream of LCK, the phosphorylation of LCK (Y394)(Nyakeriga, et al. (20120 *Cytometry A* 81:797-805), CD247 (Y142)(Weber, et al. (2019) *Blood Adv.* 3:711-717), and ZAP70 (Y319)(Williams et al. (1999) *EMBO J.* 18:1832-44) was assessed. The level of tyrosine phosphorylation at baseline across these three proteins were markedly high in dasatinib-sensitive T-ALL cases and decreased dramatically upon dasatinib treatment in a dose-dependent fashion. By contrast, there was minimal phosphorylation of LCK, CD247, and ZAP70 in dasatinib-resistant T-ALL at baseline which also did not change with increasing concentrations of dasatinib. Similar results were observed in T-ALL cell line models: dasatinib-sensitive HSB-2 cells exhibited high LCK/CD247/ZAP70 phosphorylation whereas dasatinib-resistant cell line CEM showed low phosphorylation of these three proteins. To globally explore dasatinib-mediated kinase inhibition, three sensitive and two resistant T-ALL were selected for systematic phospho-proteomic profiling. In total, 21,450 unique phosphosites were identified across samples and inferred activity of 172 human kinases based on the level of phosphorylation of their known substrates. In dasatinib-sensitive T-ALL, four kinases-LCK, LYN, FYN, and INSR-were significantly inhibited by dasatinib, whereas no kinase activation was observed using this drug. In contrast, dasatinib-resistant T-ALL cells showed no significant changes in the activity of any kinases tested before and after dasatinib treatment. Finally, because dasatinib can broadly inhibit SRC family kinases (including both SRC and LCK), these T-ALL cases, as well as cell lines, were also tested with TKIs (WH 4-023 and nintedanib) that are more specific for LCK inhibition. Both compounds showed potent cytotoxicity in dasatinib-sensitive cases whereas dasatinib-resistant T-ALL largely did not respond to these LCK-specific drugs ($P=1.1\times10^{-4}$ and $6.7\times10^{-4}$ by Pearson correlation test for WH 4-023 and nintedanib, respectively). Together, these results indicate that the anti-leukemic activity of dasatinib in T-ALL is most likely mediated by LCK inhibition.

Example 4: Genome-Scale CRISPR-Cas9 Screen Validated LCK Dependency in T-ALL

Unbiased genome-scale CRISPR-Cas9 screening was performed to identify genes essential to the growth and survival of T-ALL as compared to other cancer cell lines (Meyers, et al. (2017) *Nat. Genetics* 49:1779-1784). Comparing the three T-ALL cell lines assayed (HSB-2, PF-382, and SUP-T1) to either all other cancer cell lines screened (N=686) or limited to hematologic malignancy cell lines (N=73), LCK emerged as the top selectively essential gene. LCK dependency varied amongst three T-ALL cell lines but was dramatically higher than cells lines from any other cancer types ($P=1.4\times10^{-34}$). Interestingly, other preTCR pathway genes (e.g., CD247, ZAP70) also showed significant effects on T-ALL survival in a subset of cells, consistent with the essential role of this signaling axis in T-ALL leukemia maintenance. In contrast, deletion of SRC or other members of the SRC kinase family only minimally influenced T-ALL survival.

Example 5: Biomarker Modeling Predicted Dasatinib Sensitivity Across T-ALL Subtypes To build a robust biomarker model to predict dasatinib sensitivity in T-ALL, the top 461 driver genes identified by NetBID analysis were first filtered against preTCR pathway genes and dasatinib targets, with a final panel of 30 marker including LCK and PTCRA. Summing the weighed NetBID-inferred activity of these genes, a dasatinib sensitivity score was estimated for each T-ALL case. In the 45 T-ALL cases from the pharmacotyping cohort, dasatinib-sensitive leukemias had significantly higher scores than those resistant to this drug (average of 1.71 vs −1.32, respectively, $P=3.5\times10^{-7}$). Applying this biomarker panel to the RNA-seq dataset of 261 cases in the TARGET T-ALL cohort described above, a wide variation in predicted dasatinib sensitivity was observed across molecular subtypes. T-ALL with overexpression of TAL1, TAL2, or LMO1/2 genes exhibited the highest likelihood of dasatinib response whereas cases in the LMO2/LYL1 subtype were the least sensitive to this drug ($P<2.0\times10^{-16}$ by ANOVA). However, dasatinib response was predicted in all subtypes of T-ALL. Applying t-SNE analysis to the activity profiles of these 30 biomarker genes in the TARGET T-ALL cohort and also the pharmacotyping T-ALL dataset, four distinctive clusters were identified. The majority of dasatinib-resistant and dasatinib-sensitive cases grouped with clusters 1 and 2, respectively. Cluster 2 was also characterized by the over-representation of TAL1 T-ALL, consistent with the predicted dasatinib sensitivity in this subset. Analyzing treatment outcome of the TARGET T-ALL cohort, highly variable prognosis of these four clusters with conventional cytotoxic chemotherapy was noted. In particular, cluster 2 (enriched for the dasatinib-sensitive T-ALL) showed a significantly inferior survival than cluster 1 (enriched for dasatinib-resistant cases, P=0.02, Cox regression test), suggesting potential benefits of adding dasatinib to the ALL treatment regimen for this group of patients.

Example 6: T Cell Differentiation Program and Dasatinib Sensitivity in T-ALL

Within T-ALL cases sensitive to dasatinib, a unifying somatic genomic abnormality was not observed that completely explained this drug response phenotype, although a number of features were notable. Activating mutations in NOTCH1 were detected in 93.3% of dasatinib responders compared to 50% in drug-resistant T-ALL (P=0.0069 by Fisher's exact test), and similarly FBXW7 mutation was associated with dasatinib sensitivity (33.3% vs 6.7%, P=0.032 by Fisher's exact test). Known to be associated with early T precursor ALL, mutations in the DNM2 or RUNX1 genes were only observed in cases resistant to dasatinib, suggesting LCK signaling may be dispensable in T-ALL with this immature immunophenotype.

Most notably, TCF7-SP1 fusion was identified in one T-ALL case with exquisite sensitivity to dasatinib ($LC_{50}$=0.05 nM). Recently described as a novel subtype, TCF7-SPI1 T-ALL is associated with a characteristic expression profile, including elevated expression of PTCRA (encoding preTCRα) and LCK (Seki, et al. (2017) *Nat. Genetics* 49:1274-1281). Because upregulation of these two genes was strongly associated with dasatinib sensitivity in T-ALL, it was postulated that SPI1-rearranged T-ALL is highly susceptible to dasatinib-induced cell death. To test this, two additional T-ALL cases with the same SPI1 fusion gene were subsequently identified, and in both cases extreme ex vivo sensitivity to dasatinib ($LC_{50}$=0.05 nM) was confirmed. During normal T cell development, PTCRA expression is specifically turned on at the double negative 3a/3b (DN3a/3b) stage which in turn triggers a robust proliferative signal through LCK activation (Rothenberg, et al. (2008) *Nat. Rev. Immunol.* 8:9-21). Therefore, it was hypothesized that the differentiation arrest of TCF7-SPI1 T-ALL at DN3 stage renders them vulnerable to LCK inhibition by dasatinib. In fact, applying the 30-gene biomarker model to expression profiles of murine T cell compartments at 23 differentiation stages (Mingueneau, et al. (2013) *Nat. Immunol.* 14:619-632), it was noted that the predicted dasatinib sensitivity score rose sharply between DN2 and DN3, with a similar pattern observed for LCK and PTCRA activities. Conversely, the gene activity profile of each T-ALL case was also compared against these 23 stages during normal T cell development and quantified leukemia's similarity to different T cell compartments by clustering analysis. Across these T cell compartments, dasatinib-resistant T-ALLs were most related to the early T-cell precursor (ETP) cells whereas dasatinib-sensitive cases were clustered closely to the DN3-DN4 T cells.

To demonstrate this experimentally, mouse hematopoietic progenitor cells (LSK cells, $Lineage^{-}Sca^{+}cKit^{+}$) were isolated and transduced with either TCF7-SPI1 fusion gene or empty vector as the control. Transduced LSK cells were then allowed to differentiate into various T cell subsets in vitro in the presence of OP9-DL1 cells. While the control LSK cells differentiated extensively into mature CD4/8 single positive T cells, TCF7-SPI1-expressing LSKs were unable to differentiate beyond the DN3 stage, which showed significantly higher levels of phosphorylation of LCK. Similarly, variable dasatinib sensitivity was also observed across populations within mouse DN thymocytes: dasatinib induced robust growth inhibition of the DN3 cells and had little effects on DN1 and DN2 cells. Therefore, differentiation arrest at the DN3 stage represents a mechanism of LCK activation and dasatinib sensitivity, as exemplified in SPI1-rearranged T-ALL.

Example 7: Dynamic Shift of BCL2 and BCL-XL Dependency During T-Cell Differentiation and its Relation to T-ALL Response to Dasatinib and Venetoclax Among the top 461 driver genes for dasatinib sensitivity in T-ALL were BCL2 and BCL-XL. NetBID-inferred activity of BCL2 was significantly higher in dasatinib-resistant T-ALL than cases sensitive to dasatinib, whereas BCL-XL activity was positively associated with dasatinib response ($P=8.0\times10-7$ and $1.3\times10-7$, respectively). Similar to LCK, the activity of BCL2 and BCL-XL also shift dynamically across T-cell developmental stages. BCL2 is most up-regulated in ETP cells and its activity subdues as T cells become more mature, with the lowest value observed in the DN3-DN4 populations before it is activated again at the immature single positive (ISP) stage. By contrast, BCL-XL activity oscillates in a pattern that is opposite to BCL2, rising gradually from ETP to DN3 then followed by downregulation until T cells reach the ISP stage. Based on these observations, it was postulated that dasatinib-sensitive T-ALL would be resistant to BCL2 antagonist venetoclax because of low BCL2 activity arising from developmental arrest at the DN3-DN4 stages. Testing venetoclax sensitivity ex vivo in the pharmacotyping T-ALL cohort (N=34), dasatinib-sensitive leukemia was indeed resistant to BCL2 inhibition-induced apoptosis. Venetoclax sensitivity ex vivo was associated with high BCL2 activity, whereas high BCL-XL activity was linked to resistance to venetoclax. Consistently, LCK activity was higher in venetoclax-resistant T-ALL than—sensitive cases. To comprehensively identify biological basis for T-ALL sensitivity to venetoclax, NetBID analyses was performed and 656 driver genes with P value <0.001 were nominated, with a highly significant enrichment of genes in the preTCR signaling pathway. Each of the 7,441 genes included in the NetBID analysis were examined for their effects on sensitivity to dasatinib vs. venetoclax. A remarkable negative correlation was observed, i.e., genes driving dasatinib sensitivity were almost always associated with venetoclax resistance.

To explain the relationship between maturation stage of T-ALL and its response to dasatinib and venetoclax, activity scores of LCK, BCL2 and BCL-XL were compared in patients with different immunophentoypes in TARGET cohort. ETP T-ALL cases showed the lowest activity score for LCK and BCL-XL, compared to near-ETP and non-ETP cases. By contrast, ETPs had the highest BCL2 activity, consistent with previous report and their sensitivity to venetoclax (Chonghaile, et al. (2014) *Cancer Discovery* 4:1074-1087).

Example 8: Single-Cell RNA-Sequencing Identified Leukemia Heterogeneity in PreTCR and BCL2 Signaling, T-Cell Maturation, and Dasatinib Response ALL can exhibit complex clonal architecture with genetic heterogeneity that may directly influence drug response. In fact, subclones that escape initial therapy often give rise to ALL relapse. To explore the biological basis of intra-tumor variability in dasatinib sensitivity, single-cell RNA-sequencing (scRNA-seq) analysis was performed on two dasatinib-sensitive T-ALL cells with detectable subclones as determined by TCRβ rearrangements. For each case, leukemia cells were profiled with vs without exposure to dasatinib in vitro (i.e., incubated with dasatinib or vehicle for 96 hours, respectively), and it was postulated that cells that survived dasatinib would be drug resistant whereas vehicle-treated cells should remain naïve and drug sensitive. In SJ65, unsupervised clustering analysis of the scRNA-seq data identified three clusters, namely C1, C2, and C3, each of which consisted of both dasatinib-treated and naïve cells. By computationally inferring the dasatinib biomarker score in each cell using NetBID, strikingly, distinct dasatinib biomarker scores were observed, with C1, C2, and C3 predicted as the most sensitive, intermediate, and resistant response to dasatinib. In fact, C3 was primarily composed of naïve leukemia cells sensitive to dasatinib (35.6% of cells), and this population was largely depleted upon dasatinib treatment. By contrast, cells that survived dasatinib were predominant in the drug-resistant cluster C1, and C2 included both sensitive and resistant populations. Consistent with the biomarker analyses from bulk RNA-seq, NetBID-inferred activity of LCK was highest in the dasatinib-sensitive clusters C3 and C2 and decreased in drug resistant cluster C1, and the opposite trend was observed for BCL2. In fact, at a single cell level, there was a striking inverse correlation of LCK and BCL2 activity ($R=-0.77$, $P<2.2\times10^{-16}$), while BCL-XL and LCK activities exhibited a positive correlation ($R=0.49$, $P<2.2\times10^{-16}$). Pseudotiming analysis was also performed and indicated a C1>C2>C3 differentiation trajectory. Superimposing gene signatures of T-cell maturation stages, it was observed that a significant enrichment of ETP genes (e.g., CD34, CD44) in C1 and DN3/4 signature genes (e.g., CD3D, CD3E, CD3G, ZAP70, CD28, LEF1) in C3 suggesting that the differentiation trajectory from C1 to C3 resembled that from ETP to DN3/4 stages in T-cell differentiation. These analyses of single cell RNA-seq were repeated in the second T-ALL case and highly consistent results were observed. Taken together, these single cell profiling experiments indicated that the same biological regulators of dasatinib sensitivity identified from bulk RNAseq were also operative at the single cell level: DN3/4 stage with high LCK activity linked to sensitivity and ETP stage with high BCL2 activity linked to resistance, respectively. More importantly, the results identified subpopulations within individual T-ALL samples with heterogeneous signaling circuitry and drug response potential, which may explain the dasatinib resistance at relapse.

Example 9: In Vivo Efficacy of Dasatinib Therapy in T-ALL

Anti-leukemic efficacy of dasatinib was also demonstrated in vivo using PDX of four cases of dasatinib sensitive T-ALL. Given at 10 mg/kg twice daily, dasatinib significantly impeded leukemia growth in the recipient mice compared to those receiving vehicle control across the 4 cases, with prolonged leukemia-free survival ranging from 1.47 to 1.90-fold. However, dasatinib monotherapy did not eradicate T-ALL and disease progressed during treatment in all cases.

Integrating multi-modality molecular profiling (whole transcriptomic, genomic, and phospho-proteomics) with functional genomic screen, hyperactivation of the preTCR-LCK signaling was identified as a highly effective therapeutic target in childhood T-ALL with a significant clinical relevance for a large and high-risk patient population.

What is claimed is:

1. A method of identifying and treating a patient sensitive to treatment with a tyrosine kinase inhibitor comprising determining increased activity levels of LCK nucleic acid or protein in a biological sample isolated from a patient with a T-lineage hematological malignancy as compared to a reference level in combination with determining an increased activity level of CD28, CD3E, CD40LG, CD3G, ICOS, and/or PTCRA nucleic acids as compared to a reference level, and treating the patient exhibiting increases in the activity levels of the LCK nucleic acid or protein and an increase in the activity level of CD28, CD3E, CD40LG, CD3G, ICOS, and/or PTCRA nucleic acids as compared to reference levels with a tyrosine kinase inhibitor, thereby identifying and treating the patient sensitive to treatment with a tyrosine kinase inhibitor.

2. The method of claim 1, wherein the T-lineage hematological malignancy is T-cell acute lymphoblastic leukemia.

3. The method of claim 1, wherein the tyrosine kinase inhibitor is dasatinib or ponatinib.

4. The method of claim 1, wherein the activity of the LCK nucleic acid is determined by calculating an activity score based upon a transcriptomic profile of the patient.

5. The method of claim 1, wherein the activity of the LCK protein is determined by measuring phosphorylation levels of the LCK protein with a phospho-specific antibody via flow cytometry.

6. The method of claim 5, further comprising determining an activity level of CD247 or ZAP70 protein.

* * * * *